| United States Patent [19] | [11] | 4,231,782 |
|---|---|---|
| Franz et al. | [45] | Nov. 4, 1980 |

[54] N-CARBOBENZOXY-N-PHOSPHONOME-THYLGLYCINE THIOESTERS

[75] Inventors: John E. Franz, Crestwood; Robert J. Kaufman, University City, both of Mo.

[73] Assignee: Monsanto Company, St. Louis, Mo.

[21] Appl. No.: 957,766

[22] Filed: Nov. 3, 1978

[51] Int. Cl.³ .......................... A01N 57/12; C07F 9/40
[52] U.S. Cl. ............................................ 71/87; 71/86; 260/942; 260/940
[58] Field of Search .................... 260/942, 940; 71/86, 71/87

[56] References Cited

U.S. PATENT DOCUMENTS

| 3,197,496 | 7/1965 | Le Suer | 71/87 X |
| 3,282,991 | 11/1966 | Klein et al. | 71/115 X |
| 3,991,095 | 11/1976 | Gaertner | 71/86 X |
| 4,137,064 | 1/1979 | Trueb | 71/86 |

*Primary Examiner*—Catherine L. Mills
*Attorney, Agent, or Firm*—William T. Black; Donald W. Peterson

[57] ABSTRACT

This disclosure relates to N-phosphonomethylglycine derivatives wherein a benzoxycarbonyl group is attached to the nitrogen and alkoxy, alkenylthio, alkylthio, phenylalkylthio, phenylthio or substituted phenylthio groups are attached to the phosphorus atom and alkyl, chloroalkyl, alkoxyalkyl or alkoxyalkoxyalkyl groups are attached to the carboxyl group of the molecule. These compounds are useful as herbicides.

30 Claims, No Drawings

N-CARBOBENZOXY-N-PHOSPHONOMETHYLGLYCINE THIOESTERS

This invention relates to a new class of organic chemical compounds. More particularly, this invention is concerned with novel derivatives of N-phosphonomethylglycine wherein a benzoxycarbonyl group

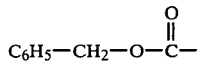

is attached to the nitrogen and alkoxy, alkylthio, substituted alkylthio, phenylthio or substituted phenylthio groups are bonded to the phosphorus atom. This class of compounds has been found to display desirable herbicidal activity when applied to certain varieties of weeds or undesired plants.

U.S. Pat. No. 3,799,758 describes the preparation of N-phosphonomethylglycine and certain of its esters, amides and salts. Also described is the use of such compounds as contact or post-emergent herbicides.

U.S. Pat. No. 3,991,095 describes derivatives of N-phosphonomethylglycine and salts thereof wherein there is a thiocarbonyl group attached to the nitrogen atom.

U.S. Patent application Ser. No. 922,900 filed July 10, 1978 describes certain thioester derivatives of N-trifluoroacetyl-N-phosphonomethylglycine.

The compounds of the present invention are represented by the formula

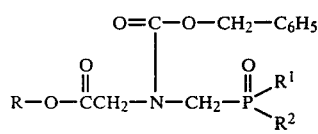

wherein R is a member of the class consisting of alkyl of from 1 to 10 carbon atoms, chloroalkyl of from 1 to 4 carbon atoms, alkoxyalkyl and alkoxyalkoxyalkyl groups and $R^1$ and $R^2$ are each a member of the class consisting of lower alkoxy, cyanoalkoxy, lower alkenylthio, alkylthio containing from 1 to 6 carbon atoms, phenylalkylthio wherein the alkyl group contains up to 4 carbon atoms, phenylthio and substituted phenylthio. It is preferred that R be alkyl of from 1 to 5 carbon atoms and even more preferred that R represent ethyl or methyl. It is preferred that $R^1$ and $R^2$ represent lower alkenylthio, alkylthio of from 1 to 6 carbon atoms, phenylalkylthio wherein the alkyl group contains up to 4 carbon atoms, phenylthio or substituted phenylthio. It is even more preferred that $R^1$ and $R^2$ be alkylthio containing from 1 to 5 carbon atoms.

As employed herein, the term "lower alkoxy" designates those alkoxy radicals which contain up through 4 carbon atoms in a straight or branched chain, e.g., methoxy, ethoxy, n- and isopropoxy, n-, sec-, iso- and tert-butoxy. By the term "substituted phenyl" as employed herein is meant a phenyl group substituted with one or two members of the class consisting of halogen, e.g., fluoro, bromo and chloro, lower alkoxy and lower alkyl, i.e., alkyl groups containing from 1 to 4 carbon atoms. Such substituted phenyl groups are, for example, chlorophenyl, fluorophenyl, bromophenyl, dichlorophenyl, chlorofluorophenyl, methylphenyl, ethylphenyl, methylchlorophenyl, methoxyphenyl, methoxychlorophenyl, methylmethoxyphenyl and the like.

Illustrative of the alkoxyalkyl groups which R represents are methoxyethyl, methoxypropyl, methoxybutyl, ethoxyethyl, ethoxypropyl, propoxyethyl, propoxypropyl and the like. Illustrative of the alkoxyalkoxyalkyl groups represented by R are, for example, methoxyethoxyethyl, methoxyethoxypropyl, methoxypropoxypropyl, methoxypropoxybutyl, ethoxyethoxyethyl, propoxypropoxypropyl and the like.

In accordance with the present invention, the compounds are prepared by reacting a dichloro compound of the formula

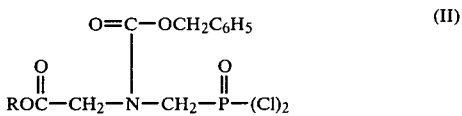

wherein R is as above defined with an alcohol or thio alcohol of the formula

wherein $R^1$ is as above defined and Z is oxygen or sulfur in the presence of a hydrogen halide acceptor such as pyridine, triethylamine, tripropylamine, tributylamine and the like at a temperature at which the dichloro compound and the alcohol or thiol react to produce the compounds of this invention (Formula I).

The reaction is generally conducted at ambient temperatures for convenience although higher and lower temperatures in the range of from 0° C. to about 75° C. can be employed if desired.

From a study of the reaction, it is obvious to those of skill in the art that at least one equivalent of the alcohol or thiol should be employed for each equivalent of phosphorus-bonded chlorine and that at least an equivalent amount of the hydrogen halide acceptor should also be employed. For ease of reaction and recovery of the product, it is preferred to employ slightly in excess of one equivalent of the alcohol or thiol and hydrogen halide acceptor for each equivalent of phosphorus-bonded chlorine.

The solvent that can be employed to produce the compounds of this invention for obvious reasons should be as dry as possible and preferably anhydrous. These solvents are generally aprotic solvents in which the reactants and products are soluble. Such solvents are, for example, diethyl ether, diisopropyl ether, tetrahydrofuran and the like.

The starting materials for the production of the compounds of this invention are prepared by the following procedure which for simplicity employs ethyl N-phosphonomethylglycine as the reagent.

Ethyl N-phosphonomethylglycine (9.85 g., 0.05 mole) and benzyl chloroformate (9.4 g., 0.05 mole) were dissolved in 50 ml. of water and sodium carbonate (7.95 g., 0.075 mole) was added over a ½ hour period. The solution was stirred until all of the benzyl chloroformate had reacted. Concentrated hydrochloric acid (12.5 ml) was then added. Upon standing ehtyl N-carbobenzoxy-N-phosphonomethylglycinate separated as an oil. The oil was then dried in a vacuum dessicator over phosphorus pentoxide at 0.55 torr. A 4 g. sample of the oil was dissolved in oxalyl chloride (20 ml) and stirred until gas evolution ceased. The mixture was concentrated in vacuo to yield ethyl N-carbobenzoxy-N-(dichlorophosphonomethyl)glycinate as a colorless oil. Other ester derivative starting materials for use in the production of the compounds of this invention are prepared by the same procedure employing the appropriate ester of N-phosphonomethylglycine. These derivatives were employed to produce the compounds in accordance with the following examples.

The following examples serve to further illustrate this invention. In the examples all parts are parts by weight unless otherwise expressly set forth.

EXAMPLE 1

Ethyl N-carbobenzoxy-N-(dichlorophosphonomethyl)-glycinate (17.5 g., 0.05 mole) was dissolved in 100 ml. of dry diethyl ether and thiolphenol (10 ml) and triethylamine (13 ml) dissolved in 100 ml. of diethyl ether was added. This reaction mixture was stirred overnight at room temperature and then filtered. The filtrate was concentrated in vacuo to yield 24 g. of a crude product. The crude product was chromatographed on silica gel (600 g.) using methyl chloride as the eluting solvent to yield ethyl N-carbobenzoxy-N-[(dithiophenyl)phosphonomethyl]glycinate as a colorless oil which gave the following analysis.

Calc'd: C, 58.24; H, 5.08; N, 2.72; P, 6.01. Found: C, 58.36; H, 5.02; N, 2.81; P, 5.89.

EXAMPLE 2

Ethyl N-carbobenzoxy-N-(dichlorophosphonomethyl)-glycinate (7.34 g., 0.02 mole) was dissolved in diethyl ether. To this solution was added triethylamine (4.04 g., 0.04 mole) and methanethiol (1.92 g., 0.04 mole) dissolved in 100 ml. of diethyl ether. The resulting solution was stirred overnight at room temperature and then filtered to remove the triethylamine hydrochloride. The ether filtrate was concentrated in vacuo to afford a yellow oil which was then extracted in petroleum ether. Upon evaporation of the petroleum ether, ethyl N-carbobenzoxy-N-[(dithiomethyl)phosphonomethyl]glycinate was obtained as a colorless oil, $N_D = 1.5580$, having the following analysis.

Calc'd: C, 46.03; H, 5.67; N, 3.58; P, 7.91. Found: C, 45.77; H, 5.54; N, 3.68; P, 7.72.

EXAMPLE 3

Ethyl N-carbobenzoxy-N-(dichlorophosphonomethyl)-glycinate (11.8 g., 0.03 mole) was dissolved in 100 ml. of diethyl ether and ethanethiol (3.98 g., 0.06 mole) and triethylamine (6.78 g., 0.06 mole) were added. The resulting mixture was stirred overnight at room temperature. The reaction mixture was then filtered to remove triethylamine hydrochloride and the filtrate concentrated in vacuo to yield an oil. The oil was dissolved in diethyl ether and chromatographed on a silica gel column to yield ethyl N-carbobenzoxy-N-[(dithioethyl)phosphonomethyl]glycinate as a light yellow oil having $N_D^{25} = 1.547$ and the following analysis.

Calc'd: C, 48.67; H, 6.25; N, 3.34; P, 7.38. Found: C, 48.56; H, 6.16; N, 3.42; P, 7.17.

EXAMPLE 4

Ethyl N-carbobenzoxy-N-(dichlorophosphonomethyl)-glycinate (11.3 g., 0.03 mole) was dissolved in 100 ml. of diethyl ether. To this solution was added n-butylthiol (6.14 g., 0.062 mole) and triethylamine (6.2 g., 0.062 mole) dissolved in 80 ml. of diethyl ether. The resulting mixture was stirred overnight at room temperature. The reaction mixture was filtered to remove triethylamine hydrochloride and the filtrate chromatographed through a silica gel column employing methylene chloride and diethyl ether as the eluants. Evaporation of the eluants under vacuum yielded ethyl N-carbobenzoxy-N-[(dibutylthio)phosphonomethyl]glycine as a yellow oil, $N_D^{25} = 1.527$ and having the following analysis.

Calc'd: C, 53.03; H, 7.21; N, 2.95; P, 6.51. Found: C, 53.10; H, 7.47; N, 2.72; P, 6.60.

EXAMPLE 5

Ethyl N-carbobenzoxy-N-(dichlorophosphonomethyl)-glycinate (13.15 g., 0.0375 mole) was dissolved in 100 ml. of diethyl ether. To this solution was added isopropylthiol (5.8 g., 0.075 mole) and triethylamine (7.575 g., 0.075 mole) dissolved in diethyl ether. The resulting solution was stirred at room temperature over a 72-hour period. The reaction mixture was then filtered and concentrated in vacuo to yield the reaction product. The reaction product was extracted into petroleum ether at room temperature and then concentrated in vacuo to yield ethyl N-carbobenzoxy-N-[bis(isopropylthio)phosphonomethyl]glycinate as a yellow oil, $N_D^{25} = 1.5325$ and having the following analysis.

Calc'd: C, 50.99; H, 6.76; N, 3.13; P, 6.92. Found: C, 50.71; H, 6.84; N, 3.00; P, 6.77.

EXAMPLE 6

Ethyl N-carbobenzoxy-N-(dichlorophosphonomethyl)glycinate (11.7 g., 0.032 mole) and 2-cyanoethanol (4.52 g., 0.064 mole) were dissolved in tetrahydrofuran (50 ml). To this solution was added triethylamine (6.42 g., 0.064 mole) in 25 ml. of tetrahydrofuran. The resultant solution was stirred overnight at room temperature. The reaction mixture was then filtered and the filtrate concentrated in vacuo to yield ethyl N-carbobenzoxy-N-[bis($\beta$-cyanoethoxy)phosphonomethyl]-glycinate as a yellow oil, $N_D^{25} = 1.05$ and having the following analysis.

Calc'd: C, 52.17; H, 5.53; N, 9.61; P, 7.08. Found: C, 51.92; H, 5.58; N, 9.62; P, 6.99.

EXAMPLE 7

Ethyl N-carbobenzoxy-N-(dichlorophosphonomethyl)-glycinate (11.8 g., 0.032 mole) was dissolved in 100 ml. of diethyl ether. The solution was treated with secondary butylthiol (5.8 g., 0.064 mole) and triethylamine (6.5 g., 0.064 mole) dissolved in 100 ml. of diethyl ether. The resulting solution was stirred for 16 hours at ambient temperatures. The reaction mixture was filtered and concentrated in vacuo. The residue was chromatographed on a silica gel column employing methylene chloride, and then with diethyl ether. The ether solution was then concentrated in vacuo to yield ethyl N-carbobenzoxy-N-[bis(1-methylpropylthio)-phosphonomethyl]glycine (3.7 g) as a yellow oil, $N_D^{25} = 1.5322$ and having the following analysis.

Calc'd: C, 53.03; H, 7.21; N, 2.95; P, 6.51. Found: C, 53.28; H, 7.32; N, 2.93; P, 6.48.

EXAMPLE 8

Ethyl N-carbobenzoxy-N-(dichlorophosphonomethyl)glycinate (8.7 g., 0.0236 mole) was dissolved in diethyl ether (100 ml). To this solution was added isobutylthiol (4.2 g., 0.0472 mole) and triethylamine (4.76 g., 0.0472 mole) dissolved in 50 ml. of diethyl ether. The resulting mixture was stirred for 16 hours at ambient temperatures. The reaction mixture was then filtered and washed with water and concentrated in vacuo to yield ethyl N-carbobenzoxy-N-[(dithioisobutyl)phosphonomethyl]glycinate as a yellow oil, $N_D^{25}=1.5280$ and having the following analysis.

Calc'd: C, 53.03; H, 7.21; N, 2.95; P, 6.51. Found: C, 53.15; H, 7.28; N, 3.02; P, 6.45.

EXAMPLE 9

Ethyl N-carbobenzoxy-N-(dichlorophosphonomethyl)glycinate (8.8 g., 0.024 mole) was dissolved in 100 ml. of diethyl ether. To this solution was added triethylamine (4.8 g., 0.48 mole) and p-chlorothiolphenol (6.8 g., 0.048 mole) dissolved in diethyl ether (50 ml). The resulting mixture was stirred for 16 hours at ambient temperatures. The reaction mixture was then filtered and the filtrate concentrated under vacuum to yield a viscous oil which was extracted with petroleum ether. The petroleum ether was evaporated off under vacuum. The residue was chromatographed on a silica gel column eluting first with methylene chloride and then with diethyl ether. The diethyl ether solution was concentrated under vacuum to give ethyl N-carbobenzoxy-N-[bis(p-chlorothiophenoxy)phosphonomethyl]glycine (4.8 g) as a light yellow oil, $N_D^{25}=1.6017$ and having the following analysis.

Calc'd: C, 51.37; H, 4.14; N, 2.40. Found: C, 51.47; H, 4.20; N, 2.39.

EXAMPLE 10

Ethyl N-carbobenzoxy-N-(dichlorophosphonomethyl)-glycinate (9.0 g., 0.025 mole) was dissolved in diethyl ether (100 ml). To this solution was added meta-methoxythiolphenol (6.9 g., 0.05 mole) dissolved in diethyl ether (50 ml). To the resulting solution was added triethylamine (4.95 g., 0.05 mole) dissolved in diethyl ether (50 ml). The resulting mixture was stirred for 16 hours at ambient temperatures and then filtered and washed with water. The ether solution was concentrated under vacuum to yield 11.8 g. of a crude product. The crude product was chromatographed on a silica gel column employing methylene chloride and then diethyl ether as the eluants. The ether solution contained the product. On concentration, the product still contained a small amount of triethylamine hydrochloride. A small portion of this product was extracted with petroleum ether and the petroleum ether solution concentrated under vacuum to yield ethyl N-carbobenzoxy-N-[bis(3-methoxythiophenyl)phosphonomethyl]-glycine as a yellow oil, $N_D^{25}=1.5918$ and having the following analysis.

Calc'd: C, 56.34; H, 5.27; N, 2.43. Found: C, 56.12; H, 5.24; N, 2.40.

EXAMPLE 11

β-chloroethyl N-carbobenzoxy-N-(dichlorophosphonomethyl)glycinate (10.4 g., 0.026 mole) was dissolved in 100 ml. of diethyl ether and added to a solution of ethanethiol (3.2 g., 0.52 mole) and triethylamine (5.2 g., 0.052 mole) dissolved in 100 ml. of diethyl ether. The reaction mixture was then stirred for 16 hours at ambient temperatures. The reaction mixture was then filtered, washed with water and the ether solution concentrated in vacuo to yield a crude product. The crude product was chromatographed on a silica gel column employing methylene chloride and diethyl ether as the eluants. The concentration of the ether solution from the column yielded 2-chloroethyl N-carbobenzoxy-N-(diethylthio)phosphonomethylglycine (2.3 g) as a yellow oil, $N_D^{25}=1.5501$ and having the following analysis.

Calc'd: C, 44.98; H, 5.55; N, 3.09. Found: C, 44.98; H, 5.58; N, 3.05.

EXAMPLE 12

Ethyl N-carbobenzoxy-N-(dichlorophosphonomethyl)glycinate (10.7 g., 0.265 mole) was dissolved in 150 ml. of diethyl ether. To this solution was added triethylamine (5.3 g., 0.53 mole) and ortho-methylthiolphenol (6.6 g., 0.053 mole). The resulting mixture was stirred for 16 hours at ambient temperatures, filtered, washed with a 5% hydrochloric acid solution and then with a brine solution. The ether solution was then dried and concentrated under vacuum to yield a crude product which was chromatographed on a silica gel column employing methylene chloride and then diethyl ether as the eluants. When the ether solution from the chromatographic column was concentrated under vacuum, 2-chloroethyl N-carbobenzoxy-N-[di(ortho-methylthiophenyl)-phosphonomethyl]glycinate was obtained as a yellow solid, m.p. 63°–69° C., having the following analysis.

Calc'd: C, 56.10; H, 5.06; N, 2.42. Found: C, 55.59; H, 5.03; N, 2.35.

EXAMPLE 13

2-Methoxyethyl N-carbobenzoxy-N-(dichlorophosphonomethyl)glycinate (9.8 g., 0.024 mole) was dissolved in 100 ml. of diethyl ether. To this solution was added thiolphenol (5.3 g., 0.048 mole) and then triethylamine (6.9 g) dissolved in 50 ml. of diethyl ether. The resulting mixture was stirred for 16 hours at ambient temperatures. The reaction mixture was filtered and the filtrate concentrated in vacuo to yield a crude product. The crude product was chromatographed on a silica gel column employing methylene chloride and diethyl ether. The ether solution obtained from the column was concentrated under vacuum overnight to yield 2-methoxyethyl N-carbobenzoxy-N-[(dithiophenoxy)phosphonomethyl]glycinate, $N_D^{25}=1.5982$ and having the following analysis.

Calc'd: C, 57.24; H, 5.17; N, 2.57. Found: C, 57.09; H, 5.12; N, 2.49.

EXAMPLE 14 n-Butyl N-carbobenzoxy-N-(dichlorophosphonomethyl)glycinate (9.5 g., 0.24 mole) was dissolved in 150 ml. of diethyl ether. To this solution was added 3-phenylpropylthiol (7.3 g., 0.48 mole) and then triethylamine (4.8 g., 0.048 mole) dissolved in 100 ml. of diethyl ether. This mixture was then stirred for 16 hours at ambient temperature, filtered to remove the triethylamine hydrochloride, washed with a 3% solution of ammonium hydroxide and then 5% hydrochloric acid and then with brine. The ether solution was dried over sodium sulfate, filtered and then concentrated under vacuum to yield a crude product. The crude product was chromatographed on a silica gel column employing methylene chloride and diethyl ether. Concentration of the ether eluant yielded n-butyl N-carbobenzoxy-N-[di(3-phenylpropylthio)phosphonomethyl]glycinate as a light yellow oil, $N_D^{25}=1.5685$ and having the following analysis.

Calc'd: C, 63.34; H, 6.44; N, 2.24. Found: C, 63.14; H, 6.82; N, 2.35.

EXAMPLE 15 n-Butyl N-carbobenzoxy-N-(dichlorophosphonomethyl)glycinate (10.5 g., 0.27 mole) was dissolved in 150 ml. of diethyl ether containing ortho-methoxythiolphenol (7.4 g., 0.53 mole) and treated with triethylamine (5.4 g., 0.53 mole). The mixture was stirred for 64 hours at ambient temperature. The reaction mixture was filtered and washed consecutively with 3% ammonium hydroxide, 5% hydrochloric acid, and then brine. The ether solution was dried over sodium sulfate and then concentrated in vacuo to yield a crude product (10.5 g). The crude product was chromatographed employing methylene chloride and diethyl ether through a silica gel column. The ether eluant was concentrated in vacuo to yield n-butyl N-carbobenzoxy-N-[di(ortho-methoxyphenylthio)phosphonomethyl]-glycine as a light yellow oil, $N_D^{25} = 1.5874$ and having the following analysis.

Calc'd: C, 57.70; H, 5.68; N, 2.32. Found: C, 57.53; H, 5.69; N, 2.48.

EXAMPLE 16

β-chloroethyl N-carbobenzoxy-N-(dichlorophosphonomethyl)glycinate (12.7 g., 0.0315 mole) and phenylmethylthiol (7.8 g., 0.63 mole) were dissolved in 100 ml. of diethyl ether. To this solution was added triethylamine (6.36 g., 0.063 mole) dropwise. The resulting mixture was stirred for 16 hours at ambient temperatures. The reaction mixture was filtered, washed with 3% ammonium hydroxide, then washed with brine, then with 5% hydrochloric acid and finally with brine. The ether extract was dried over anhydrous sodium sulfate and then the ether evaporated in vacuo to yield a crude product (15.95 g). The crude product was chromatographed through a silica gel column using methylene chloride to yield 2-chloroethyl N-carbobenzoxy-N-(dibenzylthio)phosphonomethylglycinate as a yellow oil, $N_D^{25} = 1.5918$ and having the following analysis.

Calc'd: C, 56.10; H, 5.06; N, 2.42. Found: C, 56.02; H, 5.06; N, 2.41.

EXAMPLE 17

Butyl N-carbobenzoxy-N-(dichlorophosphonomethyl)glycinate (13.25 g., 0.34 mole) and pentanethiol (6.96 g., 0.67 mole) were dissolved in 100 ml. of diethyl ether and 50 ml. of methylene chloride. Triethylamine (6.76 g) dissolved in 100 ml. of diethyl ether was then added. The reaction mixture was stirred for 16 hours at ambient temperatures and then filtered. The filtrate was washed with 3% ammonium hydroxide, then with brine, then with 5% hydrochloric acid and then the brine and the ether solution dried over sodium sulfate and then evaporated in vacuo to yield a crude product. The crude product was chromatographed through a silica gel column employing methylene chloride as the eluant. Evaporation of the methylene chloride yielded n-butyl N-carbobenzoxy-N-[di-(n-pentylthio)phosphonomethyl]glycinate as a yellow oil, $N_D^{25} = 1.5218$ and having the following analysis.

Calc'd: C, 56.47; H, 7.96; N, 2.66. Found: C, 56.06; H, 8.07; N, 2.55.

EXAMPLE 18

Ethoxyethyl N-carbobenzoxy-N-(dichlorophosphonomethyl)glycinate (10.1 g., 0.0245 mole) was dissolved in 100 ml. of diethyl ether and then 4-bromo-m-thiolcresol (9.95 g., 0.049 mole) was added. To this solution triethylamine (4.95 g., 0.49 mole) dissolved in 100 ml. of diethyl ether was added dropwise and the resulting mixture stirred for 16 hours at ambient temperatures. The reaction mixture was then filtered, washed with 3% ammonium hydroxide, 5% hydrochloric acid and then with brine and then dried over sodium sulfate. After evaporation of the ether in vacuo, a crude material was recovered. The crude material was chromatographed through a silica gel column employing methylene chloride as the eluant. The material recovered was evaporated in vacuo to yield 2-ethoxyethyl N-carbobenzoxy-N-[bis(4'-methyl-3'-bromothiophenyl)phosphonomethyl]glycinate as a yellow oil, $N_D^{25} = 1.5908$ and having the following analysis.

Calc'd: C, 46.72; H, 4.33; N, 1.88. Found: C, 46.55; H, 4.41; N, 1.81.

EXAMPLE 19

Ethoxyethyl N-carbobenzoxy-N-(dichlorophosphonomethyl)glycinate (9.15 g., 0.022 mole) was dissolved in 75 ml. of diethyl ether. To this solution was added 25 ml. of methylene chloride containing allylthiol (4.7 g., 0.44 mole) and triethylamine (4.4 g., 0.044 mole) dropwise. The reaction mixture was stirred overnight at ambient temperatures and then filtered, washed with 3% ammonium hydroxide solution, then with brine and then with a 5% hydrochloric acid solution and finally with brine. The ether solution was dried over sodium sulfate and then evaporated in vacuo to yield a crude product. The crude product was chromatographed on a silica gel column employing methylene chloride as the eluant to yield 2-ethoxyethyl N-carbobenzoxy-N-[(diallylthio)phosphonomethyl]glycinate as a yellow oil, $N_D^{25} = 1.5500$ and having the following analysis.

Calc'd: C, 51.73; H, 6.20 N, 2.87. Found: C, 51.18; H, 6.23; N, 2.78.

EXAMPLE 20

N-decyl N-carbobenzoxy-N-(dichlorophosphonomethyl)glycinate (19.7 g., 0.04 mole) was dissolved in 100 ml. of diethyl ether and methanethiol (3.9 g., 0.82 mole) was added. To this solution was added triethylamine (8.3 g., 0.082 mole) dissolved in 100 ml. of diethyl ether. The reaction mixture was stirred for 16 hours at ambient temperatures, filtered and treated as in the previous example. The crude product was chromatographed through a silica gel column employing diethyl ether as the eluant. Evaporation of the diethyl ether from the chromatographed material yielded N-decyl N-carbobenzoxy-N-[(dimethylthio)phosphonomethyl]-glycinate as a yellow oil, $N_D^{25} = 1.5242$ and having the following analysis.

Calc'd: C, 54.85; H, 7.61; N, 2.78. Found: C, 53.90; H, 7.50; N, 2.73.

EXAMPLE 21

Ethyl N-carbobenzoxy-N-(dichlorophosphonomethyl)glycinate (0.03 mole) was dissolved in diethyl ether (50 ml). The resulting solution was added to a solution of methanol (1.92 g., 0.06 mole) and triethylamine (6.06 g., 0.06 mole) and then dissolved in 100 ml. of diethyl ether. After 3 hours, the solution was filtered to remove triethylamine hydrochloride. The filtrate was washed with a sodium bicarbonate-water solution, then with 5% hydrochloric acid and finally with brine. The ether solution was dried over sodium sulfate and then concentrated in vacuo to yield ethyl N-carbobenzyoxy-N-

(dimethoxyphosphonomethyl)glycinate as an oil, $N_D^{25} = 1.4992$ and having the following analysis.

Calc'd: C, 49.45; H, 7.47; N, 3.84. Found: C, 49.43; H, 7.45; N, 3.86.

EXAMPLE 22

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the table. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the table under WAT and the results recorded. In some instances, the four-week observations are omitted.

The post-emergence herbicidal activity index used in Table I is as follows:

| Plant Response | Index |
|---|---|
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
|---|---|
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

TABLE I

| Compound of Example No. | WAT | kg/h | A | B | C | D | E | F | G | H | I | J | K |
|---|---|---|---|---|---|---|---|---|---|---|---|---|---|
| 1 | 2 | 11.2 | 1 | 0 | 0 | 0 | 1 | 1 | 0 | 0 | 0 | 0 | 1 |
| 2 | 4 | 11.2 | 1 | 2 | 1 | 1 | 2 | 2 | 1 | 2 | 3 | 2 | 2 |
| 2 | 4 | 5.6 | 1 | 1 | 1 | 1 | 2 | 1 | 0 | 1 | 1 | 1 | 2 |
| 3 | 4 | 11.2 | 1 | 1 | 1 | 1 | 1 | 2 | 1 | 2 | 3 | 2 | 2 |
| 3 | 2 | 5.6 | 1 | 0 | 0 | 0 | 0 | 1 | 1 | 0 | 1 | 0 | 1 |
| 4 | 4 | 11.2 | 1 | 1 | 1 | 1 | 1 | 0 | 1 | 1 | 1 | 1 | 1 |
| 4 | 2 | 5.6 | 0 | 0 | 1 | 0 | 0 | 0 | 0 | 0 | 0 | 0 | 1 |
| 5 | 4 | 11.2 | 1 | 1 | 1 | 1 | 2 | 1 | 1 | 2 | 2 | 2 | 2 |
| 5 | 4 | 5.6 | 1 | 1 | 1 | 1 | 1 | 1 | 0 | 1 | 1 | 1 | 1 |
| 6 | 4 | 11.2 | 2 | 1 | 1 | 1 | 2 | 2 | 0 | 0 | 0 | 0 | 1 |
| 6 | 2 | 5.6 | 0 | 0 | 0 | 0 | 0 | 1 | 0 | 0 | 0 | 0 | 1 |
| 7 | 4 | 11.2 | 1 | 1 | 0 | 1 | 1 | 1 | 1 | 1 | 2 | 1 | 2 |
| 7 | 4 | 5.6 | 1 | 1 | 0 | 1 | 1 | 1 | 0 | 1 | 1 | 0 | 1 |
| 8 | 4 | 11.2 | 1 | 1 | 0 | 1 | 2 | 0 | 0 | 0 | 1 | 0 | 1 |
| 8 | 4 | 5.6 | 1 | 0 | 0 | 1 | 1 | 0 | 0 | 1 | 1 | 1 | 1 |
| 9 | 4 | 11.2 | 0 | 1 | 0 | 0 | 1 | 1 | 0 | 0 | 0 | 0 | 1 |
| 9 | 2 | 5.6 | — | 0 | 0 | 0 | 1 | 0 | 0 | 0 | 0 | 0 | 1 |
| 10 | 4 | 11.2 | 0 | 0 | 0 | 0 | 1 | 0 | 0 | 0 | 0 | 1 | 0 |
| 10 | 4 | 56 | 0 | 0 | 0 | 2 | 1 | 2 | 0 | 0 | 0 | 0 | 1 |
| 11 | 4 | 11.2 | 0 | 0 | 1 | 0 | 0 | 0 | 0 | 0 | 0 | 1 | 1 |
| 11 | 4 | 56 | 2 | 1 | 1 | 2 | 3 | 3 | 0 | 1 | 2 | 2 | 2 |
| 12 | 2 | 56 | 0 | 0 | 0 | 1 | 0 | 0 | 0 | 0 | 0 | 0 | 0 |
| 12 | 4 | 56 | 1 | 0 | 0 | 1 | 1 | 0 | 0 | 0 | 0 | 0 | 0 |
| 13 | 2 | 11.2 | 0 | 0 | 0 | 0 | 2 | 0 | 0 | 0 | 0 | 0 | 0 |
| 13 | 4 | 56 | 0 | 2 | 0 | 2 | 3 | 2 | 1 | 1 | 0 | 0 | 2 |
| 14 | 4 | 56 | 0 | 0 | 0 | 1 | 1 | 2 | 0 | 0 | 1 | 1 | 2 |
| 15 | 4 | 56 | 2 | 2 | 1 | 2 | 4 | 4 | 2 | 2 | 4 | 1 | 3 |
| 16 | 2 | 11.2 | 0 | 0 | 0 | 0 | 0 | 0 | 0 | 0 | 0 | 0 | 1 |
| 17 | 2 | 11.2 | 0 | 0 | 1 | 0 | 0 | 0 | 0 | 0 | 0 | 0 | 1 |
| 18 | 2 | 56 | 0 | 1 | 0 | 0 | 0 | 0 | 0 | 0 | 0 | 0 | 1 |
| 19 | 2 | 11.2 | 0 | 0 | 0 | 1 | 0 | 0 | 0 | 0 | 0 | 0 | 0 |
| 20 | 4 | 11.2 | 0 | 0 | 0 | 1 | 0 | 0 | 0 | 0 | 0 | 0 | 1 |
| 20 | 2 | 5.6 | 0 | 0 | 0 | 0 | 0 | 0 | 0 | 0 | 0 | 0 | 1 |
| 21 | 4 | 56 | 0 | 0 | 0 | 2 | 2 | 0 | 0 | 0 | 0 | 0 | 0 |

From the test results presented in Table I, it can be seen that the post-emergent herbicidal activity of the compounds of this invention is, for the most part, general in nature. In certain specific instances, however, some selectivity is demonstrated. In this regard, it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent of any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent," it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 22.4 or more kilograms per hectare. In pre-emergent treatments, the rate of application can be from about 11.2 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be restored to without departing from the spirit and scope thereof and it is understood that such equivalent embodiments are intended to be included herein.

What is claimed is:

1. A compound having the formula

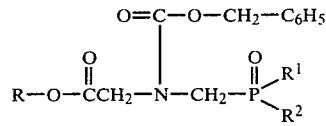

wherein R is a member of the class consisting of alkyl of from 1 to 10 carbon atoms, chloroalkyl of from 1 to 4 carbon atoms and containing from 1 to 3 chlorine atoms, alkoxyalkoxy of from 3 to 7 carbon atoms and alkoxyalkoxyalkoxy of from 5 to 9 carbon atoms and $R^1$ and $R^2$ are each selected from the class consisting of lower alkoxy, cyanoalkoxy containing from 2 to 4 carbon atoms, lower alkenylthio, alkylthio containing from 1 to 6 carbon atoms, phenylalkylthio wherein the alkyl group contains up to 4 carbon atoms, phenylthio and substituted phenylthio.

2. A compound of claim 1 wherein $R^1$ and $R^2$ are selected from the group consisting of lower alkenylthio, alkylthio containing from 1 to 6 carbon atoms, phenylalkylthio wherein the alkyl group contains up to 4 carbon atoms, phenylthio and substituted phenylthio.

3. A compound of claim 2 wherein $R^1$ and $R^2$ are alkylthio containing from 1 to 5 carbon atoms.

4. A compound of claim 3 wherein R is alkyl of from 1 to 5 carbon atoms.

5. A compound of claim 4 wherein R is ethyl.

6. A compound of claim 5 wherein $R^1$ and $R^2$ are methylthio.

7. A compound of claim 5 wherein $R^1$ and $R^2$ are ethylthio.

8. A compound of claim 5 wherein $R^1$ and $R^2$ are isopropylthio.

9. A compound of claim 5 wherein $R^1$ and $R^2$ are sec-butylthio.

10. A compound of claim 1 wherein R is ethyl and $R^1$ and $R^2$ are 2-cyanoethoxy.

11. A herbicidal composition comprising a herbicidally effective amount of a compound of claim 1 together with an inert diluent.

12. A herbicidal composition comprising a herbicidally effective amount of a compound of claim 2 together with an inert diluent.

13. A herbicidal composition comprising a herbicidally effective amount of a compound of claim 3 together with an inert diluent.

14. A herbicidal composition comprising a herbicidally effective amount of a compound of claim 4 together with an inert diluent.

15. A herbicidal composition comprising a herbicidally effective amount of a compound of claim 5 together with an inert diluent.

16. A herbicidal composition comprising a herbicidally effective amount of a compound of claim 6 together with an inert diluent.

17. A herbicidal composition comprising a herbicidally effective amount of a compound of claim 7 together with an inert diluent.

18. A herbicidal composition comprising a herbicidally effective amount of a compound of claim 8 together with an inert diluent.

19. A herbicidal composition comprising a herbicidally effective amount of a compound of claim 9 together with an inert diluent.

20. A herbicidal composition comprising a herbicidally effective amount of a compound of claim 10 together with an inert diluent.

21. A herbicidal method which comprises contacting a plant with a herbicidally effective amount of a compound of claim 1.

22. A herbicidal method which comprises contacting a plant with a herbicidally effective amount of a compound of claim 2.

23. A herbicidal method which comprises contacting a plant with a herbicidally effective amount of a compound of claim 3.

24. A herbicidal method which comprises contacting a plant with a herbicidally effective amount of a compound of claim 4.

25. A herbicidal method which comprises contacting a plant with a herbicidally effective amount of a compound of claim 5.

26. A herbicidal method which comprises contacting a plant with a herbicidally effective amount of a compound of claim 6.

27. A herbicidal method which comprises contacting a plant with a herbicidally effective amount of a compound of claim 7.

28. A herbicidal method which comprises contacting a plant with a herbicidally effective amount of a compound of claim 8.

29. A herbicidal method which comprises contacting a plant with a herbicidally effective amount of a compound of claim 9.

30. A herbicidal method which comprises contacting a plant with a herbicidally effective amount of a compound of claim 10.

* * * * *

UNITED STATES PATENT OFFICE
CERTIFICATE OF CORRECTION

PATENT NO. : 4,231,782
DATED : Nov. 4, 1980
INVENTOR(S) : John E. Franz and Robert J. Kaufman It is certified that error appears in the above-identified patent and that said Letters Patent are hereby corrected as shown below:

In Column 12, line 47, "alkoxyalkoxy" should read --alkoxyalkyl-- and in line 48 "alkoxyalkoxyalkoxy" should read --alkoxyalkoxyalkyl--.

Signed and Sealed this

Twentieth Day of September 1983

[SEAL]

Attest:

GERALD J. MOSSINGHOFF

Attesting Officer    Commissioner of Patents and Trademarks